United States Patent [19]
Crawley et al.

[11] Patent Number: 5,143,821
[45] Date of Patent: Sep. 1, 1992

[54] COLOR PHOTOGRAPHIC MATERIAL COMPRISING A 2-ALKOXY PYRAZOLO[1,5-A]BENZIMIDAZOLE COLOR COUPLER

[75] Inventors: Michael W. Crawley, Watford; Andrew W. Gibson, Woodhead, both of United Kingdom

[73] Assignee: Eastman Kodak Company, Rochester, N.Y.

[21] Appl. No.: 643,600

[22] Filed: Jan. 22, 1991

[30] Foreign Application Priority Data

Jan. 23, 1990 [GB] United Kingdom ............... 9001486

[51] Int. Cl.$^5$ ............................................. G03C 7/38
[52] U.S. Cl. .................................. 430/387; 430/386; 430/558
[58] Field of Search ............... 430/558 R, 223, 226, 430/387, 386

[56] References Cited

U.S. PATENT DOCUMENTS

| | | |
|---|---|---|
| 3,061,432 | 10/1962 | Menzel et al. ............... 430/558 |
| 3,369,897 | 2/1968 | Menzel et al. ............... 430/558 |
| 4,198,235 | 4/1980 | Vetter et al. ............... 430/222 |
| 4,237,217 | 12/1980 | Arai et al. ............... 430/558 |
| 4,704,350 | 11/1987 | Morigaki et al. ............... 430/558 |
| 4,746,599 | 5/1988 | Deguchi et al. ............... 430/504 |
| 4,755,455 | 7/1988 | Iwasa ............... 430/558 |
| 4,975,361 | 12/1990 | Sato et al. ............... 430/226 |

FOREIGN PATENT DOCUMENTS

| | | |
|---|---|---|
| 1070030 | 5/1960 | Fed. Rep. of Germany . |
| 1099349 | 8/1961 | Fed. Rep. of Germany . |
| 2156111 | 11/1971 | Fed. Rep. of Germany . |
| 5126541 | 3/1970 | Japan . |
| 2128349 | 3/1971 | United Kingdom . |
| 1546103 | 6/1972 | United Kingdom . |

Primary Examiner—Richard L. Schilling
Attorney, Agent, or Firm—Arthur E. Kluegel

[57] ABSTRACT

Novel 2-alkoxy-pyrazolo[1,5-a]benzimidazole color couplers form dyes with improved hue characteristics in photographic materials and processes. Such couplers can form magenta dyes upon oxidative coupling.

8 Claims, No Drawings

COLOR PHOTOGRAPHIC MATERIAL COMPRISING A 2-ALKOXY PYRAZOLO[1,5-A]BENZIMIDAZOLE COLOR COUPLER

This invention relates to new 4-H-pyrazolo[1,5-a]benzimidazole magenta color couplers and to photographic materials and processes comprising such couplers.

4-H-Pyrazolo-[1,5-a]benzimidazole (PBI) magenta color couplers have the basic ring structure:

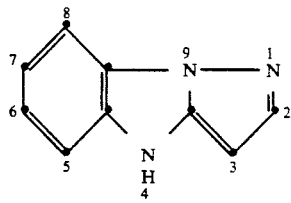

German Patent 1 070 030 describes pyrazolo[1,5-a]benzimidazole couplers which form magenta dye on coupling. Specifically the 2-octadecyl and 2-phenyl derivatives are prepared. It also describes couplers containing 2-carboxy groups while German Specification 1 099 349A describes corresponding 2-sulpho derivatives, both of which being useful to prepare Fischer type dispersions.

2-Anilino derivatives described in Japanese Specification 51/26541 and German specification 2 156 111A are said to be more active than their 2-alkyl analogues.

Pre-formed dyes containing the 4-H-pyrazolo[1,5-a]benzimidazole nucleus for use in instant photographic film units are described in the prior art containing groups in the coupling position which would not be displaced by oxidized color developer, for example Dye 7 of British Specification 1 546 103:

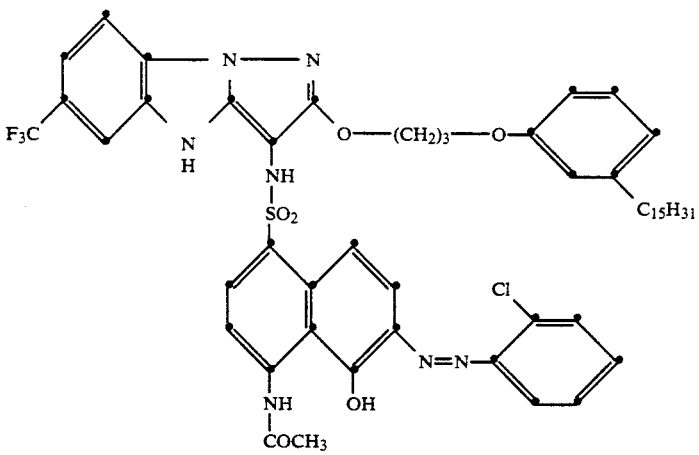

and Dye 5 in British specification 2 128 349A:

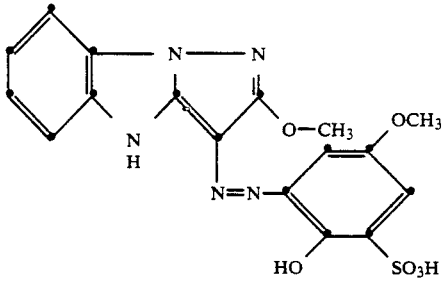

It has been desirable to provide a new class of pyrazolo[1,5-a]benzimidazole couplers that enable improved dye hue characteristics and photographic materials and processes comprising such couplers.

It has been found that photographic non-diffusible color couplers which are 2-alkoxypyrazolo[1,5-a]benzimidazoles enable formation of dyes having such improved hue characteristics. Such couplers are especially useful in a photographic element comprising a support bearing at least one photographic silver halide emulsion layer and at least one such coupler.

A preferred class of the couplers has the general formula:

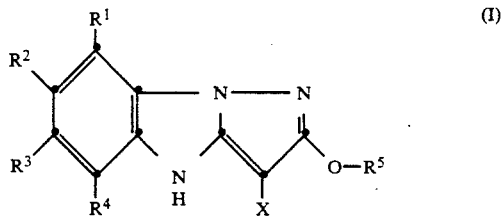

wherein $R^1$ to $R^4$ are each hydrogen or a substituent,
$R^5$ is an alkyl or substituted alkyl group, and
X is hydrogen or a coupling-off group, and wherein at least one of $R^1$ to $R^5$ or X contain a ballast group capable of rendering the coupler nondiffusible in photographic layers.

The dyes formed from the couplers have superior spectral properties compared to their 2-alkyl and 2-aryl analogues, in that the image dyes formed therefrom have a $\lambda_{max}$ of desirably shorter wavelength and a narrower half bandwidth.

$R^1$ to $R^4$ may be any substituent which is not incompatible with the intended use of the coupler. Examples of groups which $R^1$ to $R^4$ may represent are H, R [where R is alkyl (including cycloalkyl), substituted alkyl, aryl or substituted aryl], halogen (e.g., Cl, Br or F), $CF_3$, $NO_2$, CN, OH, O—R, $SO_2R$, $SO_2NR_2$, $CONR_2$, COOH, COOR, $NHSO_2R$, $NRSO_2$, NHCOR, NRCOR, $NH_2$, NHR, $NR_2$, and SR. The preferred groups are H, R, NHCOR and $NHSO_2R$.

Examples of groups which $R^5$ may represent are alkyl, especially alkyl of 1-20 carbon atoms, having a straight or branched chain which is optionally substituted with any of the substituents listed above for $R^1$ to $R^4$. Specific examples of such groups include methyl, ethyl, iso-propyl, tert-butyl, s-$C_5H_{11}$, n-$C_{12}H_{25}$, cyclohexyl, benzyl, $CH_2CH_2$-aryl, $CH_2CH_2OH$ and $CH_2COOR$.

Examples of coupling-off groups X are: H, halogen (e.g., Cl or Br), SR, S-heterocycle (e.g., phenylmercaptotetrazole) OR, $OSO_2R$, OCOR, N-containing heterocycles attached to the coupling position by the N atom (e.g., pyrazole, imidazole and triazole).

Specific examples of couplers of the present invention are listed in the following table (Me herein means methyl; Et herein means ethyl; Bu herein means butyl).

TABLE I

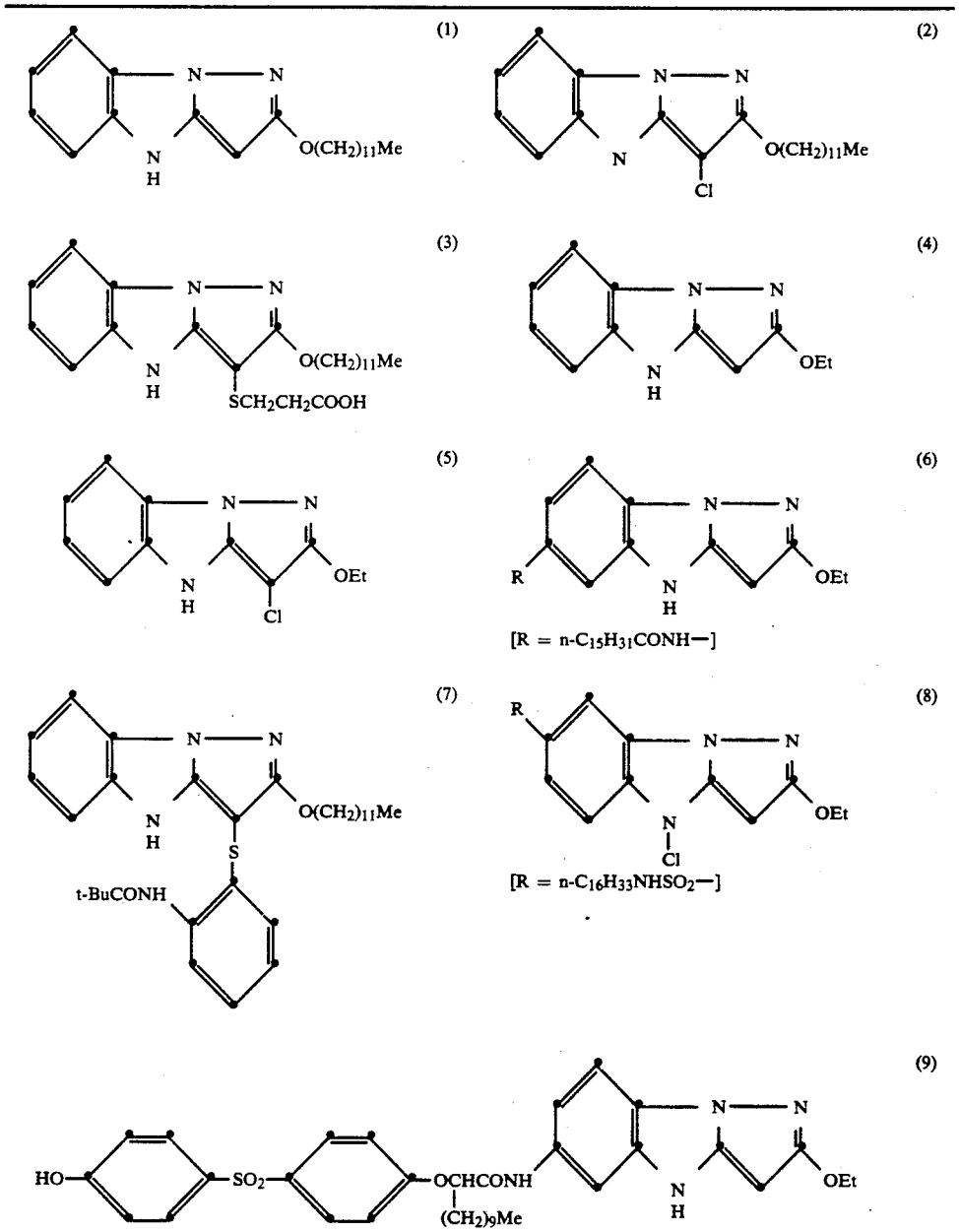

TABLE I-continued

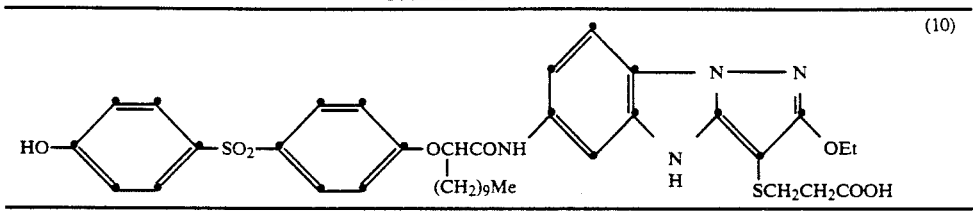

Examples of comparative couplers having 2-alkyl groups are listed in Table II below.

TABLE II

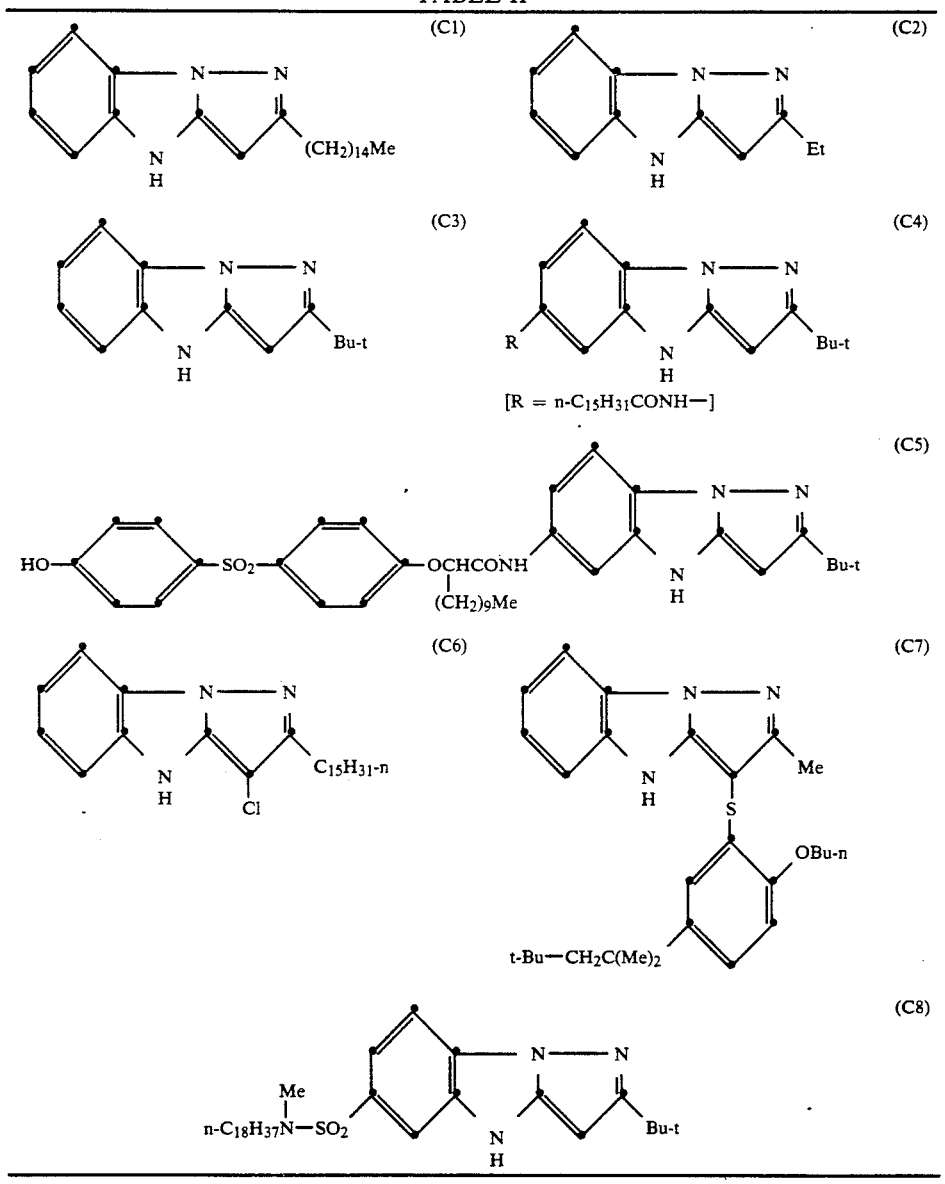

The couplers may be prepared by methods in themselves known as exemplified in the preparative Examples 3-6 below.

The dye-forming couplers of this invention can be used in the ways and for the purposes that dye-forming couplers have been previously used in the photographic art.

Typically, the couplers are associated with a silver halide emulsion layer coated on a support to form a photographic element. As used herein, the term "associated with" signifies that the coupler is incorporated in the silver halide emulsion layer or in a layer adjacent thereto where, during processing, it is capable of reacting with silver halide development products.

The photographic elements can be single color elements or multicolor elements. In a multicolor element, the magenta dye-forming couplers of this invention would usually be associated with a green-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively, at least one of the magenta dye-forming couplers being a coupler of this invention. The element can contain additional layers, such as filter and barrier layers.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methanesulphonamido)ethylaniline sulphate hydrate, 4-amino-3-methyl-N-ethyl-N-$\beta$-hydroxyethylaniline sulphate, 4-amino-3-amino-$\beta$-(methanesulphonamido)ethyl-N,N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following Examples are given for a better understanding of the invention.

EXAMPLE 1

Comparison of Dye Hues from Alkoxy Pyrazolobenzimidazole Couplers with Dye Hues from Alkyl Pyrazolobenzimidazole Couplers in Ethyl Acetate Solution.

The data in this table shows that alkoxy pyrazolobenzimidazole couplers afford dyes that are hypsochromic in dye hue to those produced by analogous or very similar alkyl PBI couplers. This is an advantages as the alkyl PBIs are too bathochromic in a conventional color negative format and the new couplers would therefore lead to better color reproduction. The couplers are arranged in groups for comparison e.g., in the first group (of two) coupler (1) of the invention is compared to comparison coupler (C1). A second advantage is the narrower half-band width (HBW) shown by the couplers of the invention, which also leads to improved color reproduction.

The two color developers used have the following formulae:

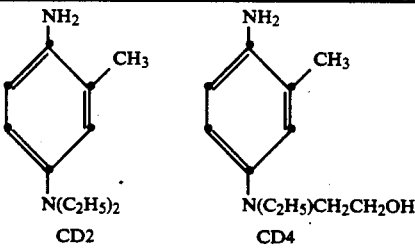

CD2    CD4

| Coupler | CD4 $\lambda$max/nm | HBW/nm | CD2 $\lambda$max/nm | HBW/nm |
| --- | --- | --- | --- | --- |
| (1) (Invention) | 535 | 80 | 530 | 81 |
| (C1) (Comparison) | 546 | 87 | 540 | 86 |
| (4) (Invention) | 534 | 82 | 530 | 82 |
| (C2) (Comparison) | 546 | 85 | 540 | 85 |
| (C3) (Comparison) | 549 | 84 | 545 | 86 |
| (6) (Invention) | 539 | 87 | 532 | 84 |
| (C4) (Comparison) | 549 | 91 | 545 | 88 |
| (9) (Invention) | 545 | 83 | 539 | 87 |

-continued

CD2: benzene ring with NH$_2$, CH$_3$, and N(C$_2$H$_5$)$_2$ substituents

CD4: benzene ring with NH$_2$, CH$_3$, and N(C$_2$H$_5$)CH$_2$CH$_2$OH substituents

| Coupler | CD4 λmax/nm | CD4 HBW/nm | CD2 λmax/nm | CD2 HBW/nm |
|---|---|---|---|---|
| (C5) (Comparison) | 557 | 83 | 553 | 84 |

EXAMPLE 2

Comparison of Dye Hues from Alkoxy Pyrazolobenzimidazole Couplers with Dye Hues from Alkyl Pyrazolobenzimidazole Couplers in Photographic Coatings.

The couplers were incorporated into a photographic silver bromoiodide emulsion and coated in the following format:

| Gel supercoat | gelatin | 1.5 gm$^{-2}$ |
|---|---|---|
| Emulsion Layer | Silver bromoiodide | 1.6 gm$^2$ |
| | Coupler | 1.04 mmolm$^2$ |
| | Gelatin | 2.42 gm$^{-2}$ |
| | Bis(vinylsulphonyl)-methane (hardener) | 0.06 gm$^{-2}$ |
| Support | Cellulose acetate | |

The couplers dispersion used contained 6% w/w gelatin, 8.8% coupler and coupler solvents in the ratio coupler:triphenyl phosphate:2-(2-butoxyethoxy)ethyl acetate 1:0.5:1.5.

On fogging and processing through a standard C-41 process, the dye hues were measured.

The table below shows photographic hue data for a selection of couplers of the invention compared to some related alkyl analogues. The same trends in dye hue are seen in this coated format as are seen in solution (Example 1).

| Coupler | CD4 λmax/nm | CD4 HBW/nm |
|---|---|---|
| (2) (Invention) | 544.5 | 100 |
| (11) (Comparison) | 558.0 | — |
| (3) (Invention) | 546.5 | 107 |
| (16) (Comparison) | 560.0 | — |
| (9) (Invention) | 558.0 | 115 |
| (10) (Invention) | 555.5 | 113 |
| (17) (Comparison) | 560.0 | 122 |
| (18) (Comparison) | 582.0 | 106 |

EXAMPLE 3

Preparation of 2-Dodecyloxy-4-H-pyrazolo[1.5-a]benzimidazole (Coupler 1)

(a) O-Dodecyl-2-ethoxycarbonylacetimidate hydrochloride.

Ethyl cyanoacetate (84.8 g, 0.75 mole) and dodecyl alcohol (140 g, 0.75 mole) were dissolved in diethyl ether (120 ml). The stirred solution was saturated with HCl gas over a period of 1.5 hrs whilst being cooled in an ice bath. A further quantity of ether was added (300 ml), and the clear solution was stirred in an ice/salt bath for 1.5 hrs to precipitate the product. The mixture was stood in a cool room at 4/C overnight, the crystalline solid filtered off, washed with a little ether, and dried under vacuum at 20/C, (yield=30.27 g.). The mass spectrum and elemental analysis results were consistent with the product being O-dodecyl-2-dodecyloxycarbonylacetimidate hydrochloride. The filtrate was placed in the fridge overnight, and this precipitated a further quantity of crystals. These were filtered off, washed with ether, and dried under vacuum at 20/C. Analysis was consistent with the desired product, O-Dodecyl-2-ethoxycarbonylacetimidate hydrochloride. The yield was 100.87 g, 40%.

Analysis; calculated for C$_{14}$H$_{34}$ClNO$_3$; Calc: C 60.8%, H 10.2%, Cl 10.6%, N 4.2%, Found: C 60.3%, H 10.1%, Cl 10.0%, N 4.1%.

(b) 3-Dodecyloxy-1-(2-nitrophenyl)pyrazol-5-one.

2-Nitrophenylhydrazine (16.1 g, 105 mmole) was stirred in tertiary butyl alcohol (150 mls), and O-dodecyl-2-ethoxy-carbonylacetimidate hydrochloride (35.0 g, 105 mmole) added with stirring. After 1.5 hr at room temperature, the formation of the intermediate hydrazone was complete. The reaction mixture was brought to reflux temperature, a solution of sodium hydroxide in water (140 ml, 0.2 g/ml) was added, and heating was continued for a further 10 min. The solution was allowed to cool and was drowned in dilute (5%) hydrochloric acid (21). The crude product was extracted into ethyl acetate, and the extracts were combined, dried with magnesium sulphate, and concentrated by rotary evaporation. The product was purified by column chromatography on silica gel, using an ethyl acetate/6-0-80/C petrol mixture (1:2) as eluant. The solid was further purified by recrystallization from ethyl acetate:60-80/C petrol (1:9) to give the product, 3-dodecyloxy-1-(2-nitrophenyl)-pyrazol-5-one, as a brown solid. The yield was 8.0 g, 20%.

Analysis; Calculated for C$_{21}$H$_{31}$N$_3$O$_4$; Calc: C 64.8%, H 8.0%, N 10.8%, Found: C 65.2%, H 8.3%, N 10.5%.

(c) 2-Dodecyloxy-4-H-pyrazolo[1,5-a]benzimidazole.

3-Dodecyloxy-1-(o-nitrophenyl)pyrazol-5-one (8.0 g, 20.54 mmole) was dissolved in acetic acid (200 ml), and 10% palladium on charcoal (0.8 g) in acetic acid (10 ml) added. The reaction mixture was hydrogenated under pressure for a period of 1.5 hrs. The catalyst was filtered from the mixture to leave a solution of the 3-alkoxy-1-(o-aminophenyl)pyrazol-5-one in acetic acid. Cyclization to (1) was effected by heating the acetic acid solution under reflux for fifteen minutes. The solution was allowed to cool, and the solvent was removed by rotary evaporation to give the crude product as a dark orange solid. Recrystallization, once from acetonitrile, and three times from an ethyl acetate/60°-80° C. ether petroleum ether mixture (1:2), gave pure 2-dodecyloxy-4-H-pyrazolo[1,5-a]benzimidazole. The yield was 3.97, 57%.

Analysis; Calculated for C$_{21}$H$_{31}$N$_3$O; Calc: C 73.9%, H 9.2%, N 12.3%, Found: C 73.7%, H 9.2%, N 12.2%.

EXAMPLE 4

Preparation of N-(2-Ethoxypyrazolo-4-H-benzimidazol-6-yl) pentadecylamide (Coupler 6)

(a) Preparation of 4-Hydrazino-3-nitrophenylpentadecanamide.

4-Fluoro-3-nitrophenylpentadecanamide (67.8 g, 0.172 mole) was dissolved in dimethyl sulphoxide (1l), and hydrazine monohydrate (20.67 g, 0.413 moles) was added in a dropwise fashion whilst keeping the temperature below 40/C. The reaction mixture was stirred for 1.5 hr at room temperature, and was then drowned in an ice/brine mixture (10l). The red solid obtained was filtered off and dried at room temperature. The product was used in this crude form without any further purification. The yield was 68.14 g, 97%.

(b) N-[3-Nitro-4-(3-Ethoxy-5-pyrazolon-1-yl)phenyl]-pentadecanamide.

N-[3-nitro-4-(3-Ethoxy-5-pyrazolon-1-yl)phenyl]pentadecanamide was prepared by the method in (3c) from 4-hydrazino-3-nitro- phenylpentadecanamide (4a) and O-ethyl 2-ethoxycarbonyl- acetimidate hydrochloride (prepared from ethyl cyanoacetate and ethanol as in method (3a) ). The yield was 49%.

Analysis; Calculated for $C_{27}H_{42}N_4O_4$; Calc: C 64.5%, H 8.4%, N 11.2%, Found: C 63.1%, H 8.4%, N 10.8%.

(c) N-(2-Ethoxypyrazolo-4H-benzimidazol-6-yl)pentadecylamide

N-(2-Ethoxypyrazolo-4H-benzimidazol-6-yl)pentadecylamide (6), was prepared from (4b) by the method indicated in (3c). The yield was 33%.

Analysis; Calculated for $C_{27}H_{42}N_4O_2$; Calc: C 71.3%, H 9.3%, N 12.3%, Found: C 71.4%, H 9.3%, N 12.1%.

EXAMPLE 5

Preparation of 2-Ethoxy-4-H-pyrazolo[1,5-a]benzimidazole, (Coupler 4)

(a) 3-Ethoxy-1-(2-nitrophenyl)pyrazol-5-one.

Finely ground ortho-nitrophenylhydrazine (2.0 g, 13.1 mmole) and ethyl-/, /-diethoxyacrylate (2.46 g, 13.1 mmole) were heated together on a steam bath for 45 minutes. Sodium metal (0.30 g, 13.1 mg-atom) was dissolved in absolute ethanol (5 ml), and the resultant solution added to the reaction mixture. Heating was continued for a further 20 min. The volume of the reaction mixture was increased to 600 ml by the addition of water, and the pH was adjusted to 4 by the addition of acetic acid. The aqueous mixture was extracted with ethyl acetate, and the crude product was purified by column chromatography on silica gel, using an ethyl acetate/60-80/C petrol mixture (1:2) as eluant. The solid was further purified by recrystallization from an ethyl acetate/petrol mixture. The yield of pure 3-ethoxy-1-(2-nitrophenyl)pyrazol-5-one was 1.63 g, 50%.

Analysis; Calculated for $C_{11}H_{11}N_3O_4$; Calc: C 53.0%, H 4.5%, N 16.9%, Found: C 53.1%, H 4.4%, N 17.0%.

(b) 2-Ethoxy-4-H-pyrazolo[1,5-a]benzimidazole

2-Ethoxy-4-H-pyrazolo[1,5-a]benzimidazole was prepared by the same route as described in (3c). The yield was 25%.

Analysis; Calculated for $C_{11}H_{11}N_3O$; Calc: C 65.7%, H 5.5%, N 20.9%, Found: C 65.5%, H 5.5%, N 20.8%.

EXAMPLE 6

Preparation of 3-(2-Dodecyloxy-4-H-pyrazolo[1,5-a]benzimidazol-3-ylthio)propionic acid. (Coupler 3)

Coupler (1) (3.91 g, 11.45 mmole) and 3-mercaptopropionic acid (1.22 g, 11.45 mmole) were stirred in dimethylformamide (60 ml), and a solution of bromine (2.93 g, 18.3 mmole) in dimethyl formamide (10 ml) was added dropwise until about a quarter of the bromine solution remained. The reaction mixture was then stirred at room temperature for two hours. The remaining bromine solution was then added in a dropwise manner, and the mixture was allowed to stir for a further thirty minutes. The solution was drowned in dilute hydrochloric acid (600 ml), and the crude product was extracted into ethyl acetate. The extracts were combined, dried with magnesium sulphate, and concentrated by rotary evaporation to give a brown oil. The crude product was purified by column chromatography on silica gel, using an ethyl acetate/60-80/C petrol mixture (1:1) as eluant. The product was further purified by recrystallization from an ethyl acetate/petrol mixture, to give pure 3-(2-dodecyloxy-4-H-pyrazolo[1,5-a]benzimidazol-3-ylthio)-propionic acid. The yield was 3.77 g, 74%.

Analysis; Calculated for $C_{24}H_{35}N_3O_3S$; Calc: C 64.7%, H 7.9%, N 9.4%, S 7.2%, Found: C 64.8%, H 7.9%, N 9.3%, S 6.8%.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and at least one dye-forming coupler which is represented by the formula:

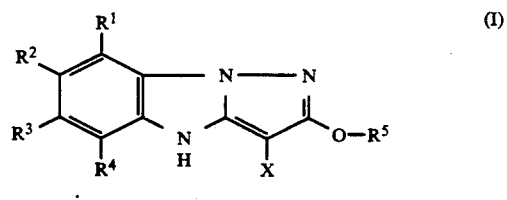

wherein $R^1$ to $R^4$ are each hydrogen or a substituent, $R^5$ is an alkyl or substituted alkyl group, and X is hydrogen or a coupling-off group selected from halogen, SR, S-heterocycle, OR, $OSO_2R$, OCOR and N-containing heterocycles attached to the coupling position by the N atom, where R is alkyl (including cycloalkyl) substituted alkyl, aryl or substituted aryl;

and wherein at least one of $R^1$ to $R^5$ or X contain a ballast group capable of rendering the coupler nondiffusible in photographic layers.

2. A photographic element comprising a support bearing at least one photographic silver halide emulsion layer and at least one dye-forming coupler selected from the group consisting of 2-dodecyloxy-4-H-pyrazolo[1,5-a]benzimidazole; N-(2-ethoxypyrazolo- 4H-benzimidazole-6-yl)pentadecylamide; 2-ethoxy-4H-pyrazolo[1,5-a]benzimidazole; and 3-(2-dodecyloxy-4H-pyrazolo[1,5-a]benzimidazole-3-ylthio)propionic acid.

3. A photographic element as in claim 1 wherein $R^1$ to $R^4$ are, independently, H, R, halogen, $CF_3$, $NO_2$, CN, OH, O—R, $SO_2R$, $SO_2NR_2$, $CONR_2$, COOH, COOR, $NHSO_2R$, $NRSO_2$, NHCOR, NRCOR, $NH_2$, NHR, $NR_2$ or SR where R is alkyl (including cycloalkyl), substituted alkyl, aryl or substituted aryl.

4. A photographic element as in claim 1 wherein $R^5$ is unsubstituted or substituted alkyl having a straight or branched chain.

5. A photographic element as in claim 1 wherein the dye-forming coupler is a non-diffusible magenta dye-forming coupler.

6. A photographic element as in claim 1 which is a multicolor photographic element comprising a support bearing yellow, magenta and cyan dye image-forming units comprising at least one blue-, green- and red-sensitive silver halide emulsion layer having associated therewith at least one yellow, magenta and cyan dye-forming coupler respectively.

7. A process of forming a dye image in an exposed photographic element comprising a support bearing a photographic silver halide emulsion, said process comprising developing the photographic element with p-phenylenediamine color developing agent in the presence of a color coupler comprising the coupler of claim 1.

8. A process of forming a dye image as in claim 8 wherein the coupler is as defined in claim 2.

* * * * *